US006872703B2

(12) United States Patent
Okano et al.

(10) Patent No.: US 6,872,703 B2
(45) Date of Patent: Mar. 29, 2005

(54) INSULIN RECEPTOR-RELATED RECEPTOR BINDING PROTEIN

(75) Inventors: Akira Okano, Kawasaki (JP); Yuzuru Eto, Kawasaki (JP); Tetsuro Izumi, Maebashi (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/874,056

(22) Filed: Jun. 6, 2001

(65) Prior Publication Data

US 2002/0192704 A1 Dec. 19, 2002

(30) Foreign Application Priority Data

Jun. 7, 2000 (JP) ........................................ 2000-170912

(51) Int. Cl.[7] ........................ C07K 14/435; A61K 38/17
(52) U.S. Cl. ................................ 514/12; 514/2; 514/8; 530/350
(58) Field of Search ............................ 530/350; 514/2, 514/8, 12

(56) References Cited

FOREIGN PATENT DOCUMENTS

| WO | WO 91/15510 | 10/1991 |
|---|---|---|
| WO | WO 93/15195 | 8/1993 |
| WO | WO 98/52607 | 11/1998 |

OTHER PUBLICATIONS

P. Shier, et al., The Journal of Biological Chemistry, vol. 264, No. 25 pps. 14605–14608, "Primary Structure of a Putative Receptor for a Ligand of the Insulin Family," Sep. 5, 1989.
I. Hirayama, et al., Diabetes, vol. 48, pps. 1237–1244, "Insulin Recetptor–Related Receptor is Expressed in Pancreatic β–Cells and Stimulates Tyrosine Phosphorylation of Insulin Receptor Substrate–1 and –2," Jun. 1999.
R. R. Reinhardt, et al., Endocrinology, vol. 133, No. 1, pps. 3–10, "Insulin Receptor–Related Receptor Messenger Ribonucleic Acid is Focally Expressed in Sympathetic and Sensory Neurons and Renal Distal Tubule Cells," 1993.
V. M. Watt, et al., Adv. Exp. Med. Biol., vol. 343, pps. 125–132, "IRR: A Novel Member of the Insulin Receptor Family," 1994.
A. Bateman, et al., Biochemical and Biophysical Research Communications, vol. 173, No. 3, pps. 1161–1168, "Granulins, a Novel Class or Peptide Form Leuckocytes," Dec. 31, 1990.
M. Shoyab, et al., Proc. Natl. Acad. Sci. USA, vol. 87, pps. 7912–7916, "Epithelins 1 and 2: Isolation and Characterization of Two Cysteine–Rich Growth–Modulating Proteins," Oct. 1990.
J. Zhou, et al., The Journal of Biological Chemistry, vol. 268, No. 15, pps. 10863–10869, "Purification of an Autocrine Growth Factor Homologous with Mouse Epithelin Precursor from a Highly Tumorligenic Cell Line," May 25, 1993.
S–Q. Xu, et al., The Journal of Biological Chemistry, vol. 273, No. 32, pps. 20078–20083, "The Granulin/Epithelin Precursor Abrogates the Requirement for the Insulin–Like Growth Factor 1 Receptor for Growth in Vitro,"Aug. 7, 1998.
J–M. Culouscou, et al., The Journal of Biological Chemistry, vol. 268, No. 14, pps. 10458–10462, "Biochemical Analysis of the Epithelin Receptor," May 15, 1993.
X. Xia, et al., Biochemical and Biophysical Research Communications, vol. 245, No. 2, pps. 539–543, "Identification of Cell Surface Binding Sites for PC–Cell–Derived Growth Factor, PCDGF, (Epithelin/Granulin Precursor) on Epithelial Cells and Fibroblasts[1]," 1998.
G. D. Plowman, et al., The Journal of Biological Chemistry, vol. 267, No. 18, pps. 13073–13078, "The Epithelin Precursor Encodes Two Proteins with Opposing Activities on Epithelial Cell Growth," Jun. 25, 1992.
V. Bhandari, et al., Proc. Natl. Acad. Sci., vol. 89, pps. 1715–1719, "Isolation and Sequence of the Granulin Precursor cDNA from Human Bone Marrow Reveals Tandem Cysteine–Rich Granulin Domains," Mar. 1992.
V. Bhandari, et al., Endocrinology, vol. 133, No. 6, pps. 2682–2689, "The Complementary Deoxyribonucleic Acid Sequence, Tissue Distribution, and Cellular Localization of the Rat Granulin Precursor," 1993.
L. M. Liau, et al., Cancer Research, vol. 60, pps. 1353–1360, "Identification of a Human Glioma–Associated Growth Factor Gene, Granulin, Using Differential Immuno–Asborption[1]," Mar. 1, 2000.

*Primary Examiner*—Prema Mertz
(74) *Attorney, Agent, or Firm*—Oblon, Spivak, McClelland, Maier & Neustadt, P.C.

(57) ABSTRACT

A protein or a variant thereof, which has a binding activity to IRR and the following characteristics and an insulin receptor-related receptor are allowed to bind in the presence of a test substance, and inhibition of the binding is measured to search for an agonist or antagonist of IRR ligand.
(a) it has the amino acid sequence of SEQ ID NO: 1;
(b) it has a molecular weight measured by mass spectrometry using the Fourier transformation ion cyclotron method of about 6135, 6206, 6250 or 6321.

11 Claims, 2 Drawing Sheets

SEQUENCE LISTING

```
<160> NUMBER OF SEQ ID NOS: 8

<210> SEQ ID NO 1
<211> LENGTH: 21
<212> TYPE: PRT
<213> ORGANISM: Mus musculus
<220> FEATURE:
<221> NAME/KEY: MISC_FEATURE
<222> LOCATION: (3)..(3)
<223> OTHER INFORMATION: X = CYS, SER, OR THR
<220> FEATURE:
<221> NAME/KEY: MISC_FEATURE
<222> LOCATION: (8)..(8)
<223> OTHER INFORMATION: X = CYS, SER, OR THR
<220> FEATURE:
<221> NAME/KEY: MISC_FEATURE
<222> LOCATION: (9)..(9)
<223> OTHER INFORMATION: X = CYS, SER, OR THR
<220> FEATURE:
<221> NAME/KEY: MISC_FEATURE
<222> LOCATION: (15)..(15)
<223> OTHER INFORMATION: X = CYS, SER, OR THR
<220> FEATURE:
<221> NAME/KEY: MISC_FEATURE
<222> LOCATION: (16)..(16)
<223> OTHER INFORMATION: X = CYS, SER, OR THR
<220> FEATURE:
<221> NAME/KEY: MISC_FEATURE
<222> LOCATION: (18)..(18)
<223> OTHER INFORMATION: X = CYS, SER, OR THR

<400> SEQUENCE: 1

Ile Gly Xaa Asp Gln His Thr Xaa Xaa Pro Val Gly Gln Thr Xaa Xaa
1               5                   10                  15

Pro Xaa Leu Lys Gly
            20

<210> SEQ ID NO 2
<211> LENGTH: 22
<212> TYPE: PRT
<213> ORGANISM: Mus musculus
<220> FEATURE:
<221> NAME/KEY: MISC_FEATURE
<222> LOCATION: (4)..(4)
<223> OTHER INFORMATION: X IS CYS, SER, OR THR
<220> FEATURE:
<221> NAME/KEY: MISC_FEATURE
<222> LOCATION: (9)..(9)
<223> OTHER INFORMATION: X IS CYS, SER, OR THR
<220> FEATURE:
<221> NAME/KEY: MISC_FEATURE
<222> LOCATION: (10)..(10)
<223> OTHER INFORMATION: X IS CYS, SER, OR THR
<220> FEATURE:
<221> NAME/KEY: MISC_FEATURE
<222> LOCATION: (16)..(16)
<223> OTHER INFORMATION: X IS CYS, SER, OR THR
<220> FEATURE:
<221> NAME/KEY: MISC_FEATURE
<222> LOCATION: (17)..(17)
<223> OTHER INFORMATION: X IS CYS, SER, OR THR
<220> FEATURE:
<221> NAME/KEY: MISC_FEATURE
<222> LOCATION: (19)..(19)
```

-continued

<223> OTHER INFORMATION: X IS CYS, SER, OR THR

<400> SEQUENCE: 2

Asp Ile Gly Xaa Asp Gln His Thr Xaa Xaa Pro Val Gly Gln Thr Xaa
1               5                   10                  15

Xaa Pro Xaa Leu Lys Gly
            20

<210> SEQ ID NO 3
<211> LENGTH: 57
<212> TYPE: PRT
<213> ORGANISM: Mus musculus

<400> SEQUENCE: 3

Asp Ile Gly Cys Asp Gln His Thr Ser Cys Pro Val Gly Gln Thr Cys
1               5                   10                  15

Cys Pro Ser Leu Lys Gly Ser Trp Ala Cys Cys Gln Leu Pro His Ala
            20                  25                  30

Val Cys Cys Glu Asp Arg Gly His Cys Cys Pro Ala Gly Tyr Thr Cys
        35                  40                  45

Asn Val Lys Ala Arg Thr Cys Gly Lys
    50                  55

<210> SEQ ID NO 4
<211> LENGTH: 57
<212> TYPE: PRT
<213> ORGANISM: Mus musculus

<400> SEQUENCE: 4

Ile Gly Cys Asp Gln His Thr Ser Cys Pro Val Gly Gln Thr Cys Cys
1               5                   10                  15

Pro Ser Leu Lys Gly Ser Trp Ala Cys Cys Gln Leu Pro His Ala Val
            20                  25                  30

Cys Cys Glu Asp Arg Gln His Cys Cys Pro Ala Gly Tyr Thr Cys Asn
        35                  40                  45

Val Lys Ala Arg Thr Cys Glu Lys Gln
    50                  55

<210> SEQ ID NO 5
<211> LENGTH: 58
<212> TYPE: PRT
<213> ORGANISM: Mus musculus

<400> SEQUENCE: 5

Asp Ile Gly Cys Asp Gln His Thr Ser Cys Pro Val Gly Gln Thr Cys
1               5                   10                  15

Cys Pro Ser Leu Lys Gly Ser Trp Ala Cys Cys Gln Leu Pro His Ala
            20                  25                  30

Val Cys Cys Glu Asp Arg Gln His Cys Cys Pro Ala Gly Tyr Thr Cys
        35                  40                  45

Asn Val Lys Ala Arg Thr Cys Glu Lys Asn
    50                  55

<210> SEQ ID NO 6
<211> LENGTH: 59
<212> TYPE: PRT
<213> ORGANISM: Mus musculus

<400> SEQUENCE: 6

Asp Ile Gly Cys Asp Gln His Thr Ser Cys Pro Val Gly Gln Thr Cys

-continued

```
                1               5                  10                 15
Cys Pro Ser Leu Lys Gly Ser Trp Ala Cys Cys Gln Leu Pro His Ala
                20                  25                  30

Val Cys Cys Glu Asp Thr Gln His Cys Cys Pro Ala Gly Tyr Thr Cys
            35                  40                  45

Asn Val Lys Ala Arg Thr Cys Glu Lys Asp Ala
            50                  55

<210> SEQ ID NO 7
<211> LENGTH: 58
<212> TYPE: PRT
<213> ORGANISM: Mus musculus

<400> SEQUENCE: 7

Ile Gly Cys Asp Gln His Thr Ser Cys Pro Val Gly Gln Thr Cys Cys
1               5                  10                  15

Pro Ser Leu Lys Gly Ser Trp Ala Cys Cys Gln Leu Pro His Ala Val
                20                  25                  30

Cys Cys Glu Asp Arg Gln His Cys Cys Pro Ala Gly Tyr Thr Cys Asn
            35                  40                  45

Val Lys Ala Arg Thr Cys Glu Lys Asp Ala
            50                  55

<210> SEQ ID NO 8
<211> LENGTH: 53
<212> TYPE: PRT
<213> ORGANISM: Mus musculus
<220> FEATURE:
<221> NAME/KEY: MISC_FEATURE
<222> LOCATION: (2)..(2)
<223> OTHER INFORMATION: X IS ANY AMINO ACID OR NONEXISTENT
<220> FEATURE:
<221> NAME/KEY: MISC_FEATURE
<222> LOCATION: (3)..(3)
<223> OTHER INFORMATION: X IS ANY AMINO ACID OR NONEXISTENT
<220> FEATURE:
<221> NAME/KEY: MISC_FEATURE
<222> LOCATION: (4)..(4)
<223> OTHER INFORMATION: X IS ANY AMINO ACID OR NONEXISTENT
<220> FEATURE:
<221> NAME/KEY: MISC_FEATURE
<222> LOCATION: (5)..(5)
<223> OTHER INFORMATION: X IS ANY AMINO ACID OR NONEXISTENT
<220> FEATURE:
<221> NAME/KEY: MISC_FEATURE
<222> LOCATION: (6)..(6)
<223> OTHER INFORMATION: X IS ANY AMINO ACID OR NONEXISTENT
<220> FEATURE:
<221> NAME/KEY: MISC_FEATURE
<222> LOCATION: (7)..(7)
<223> OTHER INFORMATION: X IS ANY AMINO ACID OR NONEXISTENT
<220> FEATURE:
<221> NAME/KEY: MISC_FEATURE
<222> LOCATION: (10)..(10)
<223> OTHER INFORMATION: X IS ANY AMINO ACID OR NONEXISTENT
<220> FEATURE:
<221> NAME/KEY: MISC_FEATURE
<222> LOCATION: (11)..(11)
<223> OTHER INFORMATION: X IS ANY AMINO ACID OR NONEXISTENT
<220> FEATURE:
<221> NAME/KEY: MISC_FEATURE
<222> LOCATION: (12)..(12)
<223> OTHER INFORMATION: X IS ANY AMINO ACID OR NONEXISTENT
<220> FEATURE:
<221> NAME/KEY: MISC_FEATURE
<222> LOCATION: (13)..(13)
<223> OTHER INFORMATION: X IS ANY AMINO ACID OR NONEXISTENT
<220> FEATURE:
<221> NAME/KEY: MISC_FEATURE
<222> LOCATION: (16)..(16)
```

```
<223> OTHER INFORMATION: X IS ANY AMINO ACID OR NONEXISTENT
<220> FEATURE:
<221> NAME/KEY: MISC_FEATURE
<222> LOCATION: (17)..(17)
<223> OTHER INFORMATION: X IS ANY AMINO ACID OR NONEXISTENT
<220> FEATURE:
<221> NAME/KEY: MISC_FEATURE
<222> LOCATION: (18)..(18)
<223> OTHER INFORMATION: X IS ANY AMINO ACID OR NONEXISTENT
<220> FEATURE:
<221> NAME/KEY: MISC_FEATURE
<222> LOCATION: (19)..(19)
<223> OTHER INFORMATION: X IS ANY AMINO ACID OR NONEXISTENT
<220> FEATURE:
<221> NAME/KEY: MISC_FEATURE
<222> LOCATION: (20)..(20)
<223> OTHER INFORMATION: X IS ANY AMINO ACID OR NONEXISTENT
<220> FEATURE:
<221> NAME/KEY: MISC_FEATURE
<222> LOCATION: (21)..(21)
<223> OTHER INFORMATION: X IS ANY AMINO ACID OR NONEXISTENT
<220> FEATURE:
<221> NAME/KEY: MISC_FEATURE
<222> LOCATION: (22)..(22)
<223> OTHER INFORMATION: X IS ANY AMINO ACID OR NONEXISTENT
<220> FEATURE:
<221> NAME/KEY: MISC_FEATURE
<222> LOCATION: (23)..(23)
<223> OTHER INFORMATION: X IS ANY AMINO ACID OR NONEXISTENT
<220> FEATURE:
<221> NAME/KEY: MISC_FEATURE
<222> LOCATION: (26)..(26)
<223> OTHER INFORMATION: X IS ANY AMINO ACID OR NONEXISTENT
<220> FEATURE:
<221> NAME/KEY: MISC_FEATURE
<222> LOCATION: (27)..(27)
<223> OTHER INFORMATION: X IS ANY AMINO ACID OR NONEXISTENT
<220> FEATURE:
<221> NAME/KEY: MISC_FEATURE
<222> LOCATION: (28)..(28)
<223> OTHER INFORMATION: X IS ANY AMINO ACID OR NONEXISTENT
<220> FEATURE:
<221> NAME/KEY: MISC_FEATURE
<222> LOCATION: (29)..(29)
<223> OTHER INFORMATION: X IS ANY AMINO ACID OR NONEXISTENT
<220> FEATURE:
<221> NAME/KEY: MISC_FEATURE
<222> LOCATION: (30)..(30)
<223> OTHER INFORMATION: X IS ANY AMINO ACID OR NONEXISTENT
<220> FEATURE:
<221> NAME/KEY: MISC_FEATURE
<222> LOCATION: (31)..(31)
<223> OTHER INFORMATION: X IS ANY AMINO ACID OR NONEXISTENT
<220> FEATURE:
<221> NAME/KEY: MISC_FEATURE
<222> LOCATION: (34)..(34)
<223> OTHER INFORMATION: X IS ANY AMINO ACID OR NONEXISTENT
<220> FEATURE:
<221> NAME/KEY: MISC_FEATURE
<222> LOCATION: (36)..(36)
<223> OTHER INFORMATION: X IS ANY AMINO ACID OR NONEXISTENT
<220> FEATURE:
<221> NAME/KEY: MISC_FEATURE
<222> LOCATION: (37)..(37)
<223> OTHER INFORMATION: X IS ANY AMINO ACID OR NONEXISTENT
<220> FEATURE:
<221> NAME/KEY: MISC_FEATURE
<222> LOCATION: (42)..(42)
<223> OTHER INFORMATION: X IS ANY AMINO ACID OR NONEXISTENT
<220> FEATURE:
<221> NAME/KEY: MISC_FEATURE
<222> LOCATION: (43)..(43)
<223> OTHER INFORMATION: X IS ANY AMINO ACID OR NONEXISTENT
<220> FEATURE:
<221> NAME/KEY: MISC_FEATURE
<222> LOCATION: (44)..(44)
<223> OTHER INFORMATION: X IS ANY AMINO ACID OR NONEXISTENT
<220> FEATURE:
<221> NAME/KEY: MISC_FEATURE
```

```
<222> LOCATION: (45)..(45)
<223> OTHER INFORMATION: X IS ANY AMINO ACID OR NONEXISTENT
<220> FEATURE:
<221> NAME/KEY: MISC_FEATURE
<222> LOCATION: (47)..(47)
<223> OTHER INFORMATION: X IS ANY AMINO ACID OR NONEXISTENT
<220> FEATURE:
<221> NAME/KEY: MISC_FEATURE
<222> LOCATION: (48)..(48)
<223> OTHER INFORMATION: X IS ANY AMINO ACID OR NONEXISTENT
<220> FEATURE:
<221> NAME/KEY: MISC_FEATURE
<222> LOCATION: (49)..(49)
<223> OTHER INFORMATION: X IS ANY AMINO ACID OR NONEXISTENT
<220> FEATURE:
<221> NAME/KEY: MISC_FEATURE
<222> LOCATION: (50)..(50)
<223> OTHER INFORMATION: X IS ANY AMINO ACID OR NONEXISTENT
<220> FEATURE:
<221> NAME/KEY: MISC_FEATURE
<222> LOCATION: (51)..(51)
<223> OTHER INFORMATION: X IS ANY AMINO ACID OR NONEXISTENT
<220> FEATURE:
<221> NAME/KEY: MISC_FEATURE
<222> LOCATION: (52)..(52)
<223> OTHER INFORMATION: X IS ANY AMINO ACID OR NONEXISTENT
<220> FEATURE:
<221> NAME/KEY: MISC_FEATURE
<222> LOCATION: (9)..(9)
<223> OTHER INFORMATION: X IS ANY AMINO ACID OR NONEXISTENT

<400> SEQUENCE: 8

Cys Xaa Xaa Xaa Xaa Xaa Xaa Cys Xaa Xaa Xaa Xaa Xaa Cys Cys Xaa
1               5                   10                  15

Xaa Xaa Xaa Xaa Xaa Xaa Xaa Cys Cys Xaa Xaa Xaa Xaa Xaa Xaa Cys
                20                  25                  30

Cys Xaa Asp Xaa Xaa His Cys Cys Pro Xaa Xaa Xaa Xaa Cys Xaa Xaa
        35                  40                  45

Xaa Xaa Xaa Xaa Cys
    50
```

INSULIN RECEPTOR-RELATED RECEPTOR BINDING PROTEIN

TECHNICAL FIELD

The present invention relates to a therapeutic agent for regulating cellular growth/differentiation and a method for searching for such a therapeutic agent. More specifically, the present invention relates to a therapeutic agent for regulating growth/differentiation of cells involved in diabetes, neuropathy, renal disorder, gastrointestinal injury and so forth and a method for searching for such a therapeutic agent.

BACKGROUND ART

Many growth/differentiation factor receptors are composed of an intracellular kinase domain and an extracellular ligand-binding domain. These receptors are classified into some families based on the similarity of domain-structures.

Recent genomic information has revealed many novel genes that are considered to encode receptors based on their structures. These genes are referred to as orphan receptors since their ligands are unidentified. However, from the information about the function of ligands for known family receptors and specificity of expression sites of these orphan receptors, it is expected that some of their ligands are important physiological factors for controlling biological functions.

Insulin receptor-related receptor (hereafter, also referred to as "IRR") is one of the orphan receptors belonging to an insulin receptor family (Shier et al., *J. Biol. Chem.*, 264: 14605, 1989). Known insulin family members such as insulin and insulin-like growth factor (IGF)-1 bind to their corresponding receptors as ligands and regulate functions such as growth of cells expressing the receptors, expression of glucose transporter and suppression of the hepatic gluconeogenesis pathway via auto-phosphorylation of the receptors. Therefore, it is expected that growth/differentiation and functions of IRR expressing cells can be regulated by using an IRR ligand via binding to IRR and phosphorylation of IRR. However, there has been reported that known insulin family members such as insulin and IGF-1 cannot bind to IRR nor induce signal transduction for phosphorylation of IRR (Zhang et al., *J. Biol. Chem.*, 267: 18320, 1992). Thus, the identity of a ligand specifically binding to IRR has remained unknown.

Increased insulin resistance such as obesity attributable to changes in life style is a major cause of the recent increase in the number of type-2 diabetes patients. On the other hand, it has also been reported that diabetes does not develop when compensatory growth/differentiation of the β cells, which are insulin secreting cells existing in the islets of Langerhans in the pancreas, occurs in response to insulin resistance (Terauchi et al., *J. Clin. Invest.*, 99: 861, 1997). Although a physiological mechanism for regulating mass of the pancreatic β cells is unknown, elucidation of its regulatory factor will provide novel preventive and therapeutic methods that increase or maintain the endogenous or transplanted pancreatic β cell mass in a diabetes patient.

In recent years, based on findings in knockout mice lacking IRS-2, which is one of intracellular substrates of insulin receptor kinase, it has been found that IRS-2 is essential to increase of the pancreatic β cell mass corresponding to an amount of insulin demand. Since then, involvement of the insulin receptor family has been strongly suggested (Withers et al., *Nature*, 391: 900, 1998). On the other hand, it has been confirmed that IRR is highly expressed in the pancreatic β cells. Further, it has also been confirmed by using an artificially prepared insulin receptor (IR)/IRR chimeric receptor, that IRR kinase phosphorylates IRS-2 (Hirayama et al., *Diabetes*, 48: 1237, 1999). And thus it is estimated that an unknown ligand binding to IRR (IRR ligand) acts on the pancreatic β cells as a factor for inducing growth, differentiation and survival of the cells. Therefore, means and a method for regulating growth/differentiation of pancreatic β cells will be provided by obtaining the IRR ligand or an agonist thereof, and it is also expected that it serves as a therapeutic agent for diabetes via regulation of growth/differentiation of the pancreatic β cells when it is administered to an living body.

Moreover, since it has been reported that IRR is expressed in specific localized tissues and cells such as nerves, kidney and stomach (Reinhardt et al., *Endocrinology*, 133: 3, 1993; Watt et al., *Adv. Exp. Med. Biol.*, 343: 125, 1993), IRR is also considered to be involved in growth/differentiation of these cells. Therefore, it is also expected that, if the IRR ligand or an agonist thereof is used to induce growth/differentiation of cells in these tissues, it will also be useful as a therapeutic agent for congenital or acquired neuropathy, renal disorder, gastrointestinal injury due to medication, autoimmunity, inflammation or the like.

Further, it is expected that an antagonist of the IRR ligand can be a therapeutic agent for diseases attributable to or accompanied with hyperplasia or hyperactivity of the aforementioned tissues or cells, for example, proliferative nephritis.

As described above, however, the IRR ligand has not been identified and there is no method for conveniently searching for its agonist or antagonist since the IRR ligand is unidentified.

Meanwhile, epithelins/granulins are known as factors for inhibiting growth of tumor cells (Shoyab et al., *Proc. Natl. Acad. Sci. USA*, 87: 7912, 1990) or as cysteine-rich proteins existing in leukocyte granules (Bateman et al., *Biochem. Biophys. Res. Commun.*, 173: 1161, 1990). As epithelins/granulins, there have been known seven kinds of them in total including granulin A (epithelin 1), B (epithelin 2), and C to G.

As functions and uses of polypeptides belonging to the epithelins/granulins, there have been described a tumor cell growth inhibiting action, epithelial cell growth accelerating action (acceleration of wound healing) and keratinocyte growth accelerating action (treatment of psoriasis with an antagonist) of epithelins 1 and 2 (Shoyab et al., *Proc. Natl. Acad. Sci. USA*, 87:7912, 1990; WO91/15510A). There has also been reported that the epithelin/granulin precursors themselves (PCDGF, GP88) accelerate growth of tumor cells and fibroblasts (Zhou et al., *J. Biol. Chem.*, 268: 10863, 1993; Xu et al., *J. Biol. Chem.*, 273: 20078, 1998; WO 98/52607). Further, there have been suggested that epithelin 1 binds to a 140–145 kDa protein on a human breast cancer cell membrane (Culouscou et al., *J. Biol. Chem.*, 268: 10458, 1993) and that PCDGF binds to a 120 kDa protein on the membrane of a mink lung epithelial cell strain (Xia et al., *Biochem. Biophys. Res. Commun.*, 245: 539, 1998). However, proteins to which these epithelin 1 and PCDGF bind have not been identified. Thus, receptors of epithelins/granulins still remain unknown, and there has been no report suggesting their association with IRR.

DISCLOSURE OF THE INVENTION

The present invention was accomplished in view of the above, and its major object is to identify an IRR ligand unknown thus far and to provide its use and a method for searching for an agonist or antagonist of the IRR ligand.

As a result of the present inventors' efforts devoted to achieve the aforementioned object, they successfully purified a protein having activity of specifically binding to IRR from a cell culture supernatant and identified this protein. Thus, they accomplished the present invention.

Specifically, culture supernatants of 76 kinds of cells stimulated with a phorbol ester were collected and concentrated, and they were screened by the surface plasmon resonance (SPR) method for those exhibiting IRR-specific binding. As a result, IRR-specific binding activity was observed in eight kinds of cell culture supernatants. Among them, rat C6 glioma cells (ATCC No. CCL-107) were cultured in a large quantity, and the culture supernatant was collected, roughly fractionated and then purified by reverse phase HPLC in three steps using IRR-specific binding activity as a marker. Then, the N-terminal amino acid sequences of the purified proteins were determined and their molecular weights were measured by mass spectrometry to identify corresponding proteins based on information of a database. As a result, it was found that the purified proteins were proteins belonging to the epithelins/granulins, which were composed of 57–59 amino acids represented by the amino acid sequences of SEQ ID NOS: 3–7 and had molecular weights of 6135, 6206, 6250 and 6321, respectively.

That is, the present invention provides the followings.
(1) A protein or a variant thereof, which has a binding activity to an insulin receptor-related receptor and the following characteristics:
(a) it has the amino acid sequence of SEQ ID NO: 1;
(b) it has a molecular weight of about 6135, 6206, 6250 or 6321 measured by mass spectrometry using the Fourier transformation ion cyclotron method.
(2) The protein according to (1), which has the amino acid sequence of any one of SEQ ID NOS: 3–7.
(3) A pharmaceutical composition, which comprises a protein binding to an insulin receptor-related receptor or an agonist or antagonist thereof as an active ingredient.
(4) The pharmaceutical composition according to (3), wherein the composition has an action of regulating growth/differentiation of a cell which expresses an insulin receptor-related receptor.
(5) The pharmaceutical composition according to (4), wherein the cell is a cell related in diabetes, neuropathy, renal disorder or gastrointestinal injury.
(6) The pharmaceutical composition according to (5), wherein the cell is a pancreatic β cell.
(7) The pharmaceutical composition according to any one of (3)–(6), wherein the protein binding to an insulin receptor-related receptor is an epithelin/granulin.
(8) The pharmaceutical composition according to (7), wherein the epithelin/granulin is a protein which is contained in a culture supernatant of rat glioma cells stimulated with a phorbol ester and concentrated in a fraction eluted with 8–20% acetonitrile from a C18 reverse phase HPLC column.
(9) The pharmaceutical composition according to (7), wherein the epithelin/granulin has the amino acid sequence of SEQ ID NO: 8.
(10) The pharmaceutical composition according to (7), wherein the epithelin/granulin is a protein having the amino acid sequence of any one of SEQ ID NOS: 3–7 or a variant thereof having a binding activity to the insulin receptor-related receptor.
(11) A DNA encoding the protein according to (1).
(12) The DNA according to claim 11, which encodes an amino acid sequence of any one of SEQ ID NOS: 3–7.
(13) A method for searching for an agonist or an antagonist of an insulin receptor-related receptor binding protein, comprising the steps of allowing binding of the insulin receptor-related receptor and a protein binding to the receptor in the presence of a test substance, and measuring inhibition of the binding.
(14) The method for searching for an agonist or antagonist of an insulin receptor-related receptor binding protein according to (13), wherein binding of the insulin receptor-related receptor and the protein binding to the receptor is detected based on shift change in surface plasmon resonance to measure inhibition of the binding.

According to the present invention, there can be provided an epithelin/granulin protein that regulates growth/differentiation of pancreatic β cells and cells in nerves, kidney, stomach and intestines as an IRR ligand.

The present invention can also provide a method for searching for an agonist or an antagonist of an IRR ligand.

Hereafter, the present invention will be explained in detail.

The IRR ligand of the present invention is a protein that specifically binds to IRR.

The IRR ligand of the present invention may be purified from, for example, as described in the examples described later, a culture supernatant of rat C6 glioma cells by reverse phase HPLC or other means, or may be synthesized by a peptide synthesis method. Also, genes corresponding to the amino acid sequences may be obtained by a method well known to those skilled in the art and used for the preparation of the ligand in bacteria, yeast, insect cells, mammalian cells or the like by a genetic recombination method. The amino acid sequences of SEQ ID NO: 3–7 were obtained by amino acid sequencing and mass spectrometry of the IRR ligand purified from a culture supernatant of the rat C6 glioma cells.

The IRR ligand of the present invention may be derived from rat, or other mammals such as human, monkey, mouse, dog, bovine or rabbit, birds, fishes or any other animals, so long as the ligand has the characteristic of binding to IRR. However, when the IRR ligand is used as an ingredient of a pharmaceutical composition, one derived from a mammal is preferred.

Further, in addition to the IRR ligand protein identified in the examples, the IRR ligand may be one having an amino acid sequence of SEQ ID NO: 8 or any one of SEQ ID NOS: 3–7 including substitution, deletion, insertion, addition or inversion of one or several amino acid residues at one or more positions so long as the ligand has the characteristic of binding to IRR. In the present invention, the term "variant" refers to one including such substitution, deletion, insertion or addition of an amino acid residue or residues or one having modification.

Further, the IRR ligand of the present invention may be a ligand in which one or several identical or different proteins are bound in tandem so long as the ligand has the characteristic of binding to IRR. The ligand may also be a ligand to which a sugar chain is bound or not bound, so long as the ligand has the characteristic of binding to IRR.

When the N-terminal amino acid sequence of the IRR ligand purified in the examples described later was searched in a database, the amino acid sequence matched the 440–460th amino acid residues of the amino acid sequence encoded by a gene known as a gene coding for rat epithelin/granulin precursor. Therefore, it was estimated that the ligand was a protein corresponding to the granulin D domain (Bhandari et al., *Proc. Natl. Acad. Sci. USA*, 89:1715, 1992). Further, the data of mass spectrometry by the Fourier transformation ion cyclotron method of newly purified IRR-ligand (6135, 6250, 6321 or 6206) revealed that the IRR ligand obtained from the culture supernatant of the rat C6 cells was a protein composed of 57–59 amino acid residues among the amino acid residues at positions of 439–497 of the epithelin/granulin precursor, which had the aspartic acid at a position of 439 or isoleucine at a position of 440 as the N-terminus, the lysine at a position of 495, aspartic acid at a position of 496 or alanine at a position of 497 as the C-terminus, and six intracellular Cys-Cys bonds.

Hereafter, epithelins/granulins will be briefly explained. Epithelins are proteins purified from rat kidney as factors inhibiting growth of tumor cells (Shoyab et al., *Proc. Natl. Acad. Sci. USA*, 87: 7912, 1990). Granulins are proteins purified as cysteine-rich proteins existing in human leukocyte granules (Bateman et al., *Biochem. Biophys. Res. Commun.*, 173: 1161, 1990). By cloning epithelin/granulin cDNA, it has been revealed that the cDNA codes for a precursor common to the epithelin/granulin group and that it contains total seven cysteine-rich motifs including granulin A (epithelin 1), B (epithelin 2), and C to G in tandem. It has also been disclosed that a region of the rat epithelin precursor consisting of the amino acid residues 440–495 (Plowman et al., *J. Biol. Chem.*, 267: 13073, 1992; WO91/15510A) or 438–492 (granulin D; Bhandari et al., *Endocrinology*, 133: 2682, 1993) is one of the motifs. There has also been disclosed, in the aforementioned reference (WO91/15510A), a structure composed of $CX_{5-6}CX_5CCX_8CCX_6CCXDXXHCCPX_4CX_{5-6}C$ (SEQ ID NO: 8) as a common structure of epithelins/granulins and two of arbitrary amino acid sequences added before and after the foregoing sequence. The IRR ligand purified in the examples had this common structure shown in SEQ ID NO: 8.

From the above, it is estimated that other granulins/epithelins or mutants thereof also bind to IRR, so long as they are, specifically, epithelin/granulin proteins represented as $CX_{5-6}CX_5CCX_8CCX_6CCXDXXHCCPX_4CX_{5-6}C$, for example.

In the present invention, the IRR ligand is not limited to those having an amino acid sequence of SEQ ID NO: 8 or SEQ ID NOS: 3–7. The IRR ligand collectively refers to proteins binding to IRR including those described above. The DNA of the present invention includes DNAs coding for such IRR ligands.

The reported and disclosed granulin D is estimated to be a homodimer or heterodimer (Bateman et al., *Biochem. Biophys. Res. Commun.*, 173: 1161, 1990; WO 93/15195). However, the result of the mass spectrometry showed that the IRR ligand purified in the present invention was a monomer not having an intermolecular bond.

Determination of active fractions in the purification of the IRR ligand from a supernatant of cells expressing the IRR ligand including the rat C6 glioma cells or identification of granulins/epithelins or mutants thereof as IRR ligands can be carried out by measuring activity for binding to IRR in a sample. The binding activity to IRR of a sample specimen can be measured by using a surface plasmon resonance (SPR) measuring apparatus, for example, BIACORE (produced by Biacore). Specifically, for example, the extracellular domain of IRR is prepared as a soluble protein and immobilized on a surface of a BIACORE sensor chip. A sample specimen is sent onto the surface of the sensor chip via a micro flow system at a constant flow rate. If a molecule binding to IRR (IRR ligand) is contained in the sample specimen, the mass of the surface sensor chip is increased due to binding between IRR and IRR ligand molecules, and a shift of the SPR signal in proportion to the binding quantity can be detected as a change in the resonance unit (RU). The IRR-specific binding can be confirmed by concurrently preparing a sensor chip having an immobilized protein other than IRR and deducting the change in the resonance unit when the sample specimen is allowed to flow onto this chip to exclude a so-called bulk effect by a solvent or the like. When, for example, an insulin receptor (IR) protein is used as a protein other than IRR, IRR-binding activity can be measured more precisely.

The soluble IRR protein used for the search can be prepared by using IRR cDNA as in the case of producing a protein by a usual genetic recombination method. For example, mouse IRR cDNA can be obtained by cloning it from a pancreatic β cell strain bHC9 or MIN6 cDNA library using, as a probe, a cDNA fragment in the kinase region of mouse IRR amplified by PCR according to the method described in Hirayama et al., *Diabetes*, 48: 1237, 1999, for example. When a soluble IR protein is used as a control, IR cDNA can be obtained from a human renal cDNA library by using a synthetic oligonucleotide as a probe according to the method described in Whittaker et al., *Proc. Natl. Acad. Sci. USA*, 84: 5237, 1987, for example.

When IRR or IR is obtained as a soluble protein, it can be obtained as follows. That is, a fragment coding for the extracellular region is obtained from the IRR cDNA or IR cDNA and introduced into an expression vector using an appropriate synthetic oligonucleotide as an adapter or spacer as required and an appropriate host is transfected with it. After the host is cultured for an appropriate time, a target protein can be purified from disrupted cell solution or culture supernatant. It is also preferable to prepare a fusion protein of IRR or IR and the H chain constant region (Fc region) of IgG, alkaline phosphatase, FLAG or the like, since it enables simpler purification of the target protein. As for IgG cDNA, for example, as described in Nishimura et al., *Cancer Res.*, 47: 999, 1987, the human IgG1 chain can be obtained from the human plasma leukemia cell strain ARH77. For example, when an IRR-Fc or IR-Fc fusion protein is prepared, a DNA fragment containing a sequence for the extracellular region (1–920th residues) of the mouse IRR or extracellular region (1–944th residues) of the human IR and a DNA fragment containing a sequence for the H chain C (constant) region (Fc region) of the human IgG1 is incorporated into an expression vector pEF-BOS (Mizushima et al., *Nucleic Acid Res.* 18: 5322, 1990) to construct a plasmid. This plasmid is transfected into CHO cells in a conventional manner and the cells are cultured in a medium containing G418 to select a resistant clone. Then, culture supernatant of the clone is loaded onto a protein A column and adsorbed fractions can be collected to obtain the target IRR-Fc fusion protein or IR-FC fusion protein.

The IRR ligand of the present invention specifically binds to IRR of cells expressing IRR thereon such as pancreatic β cells and has activity of regulating growth/differentiation of those cells. Therefore, it is considered that the IRR ligand or an agonist or antagonist thereof can be used as a therapeutic agent for diabetes, neuropathy, renal disorder and gastrointestinal injury, because it suppresses or accelerates growth/differentiation of cells involved in these diseases.

As described above, onset of type-2 diabetes requires both of insulin hyposecretion and insulin resistance, and it has been suggested that, when compensatory growth of β cells occurs, a mouse does not develop diabetes in spite of its insulin resistance. There have also been reported that those who have obesity causing insulin resistance but have not developed diabetes have more pancreatic β cells than diabetes patients. In other words, it is estimated that compensatory growth of β cells may be insufficient in diabetes patients. Therefore, if the β cell compensatory growth mechanism can be artificially accelerated to accelerate growth/regeneration of β cells and/or induce survival/maintenance of β cells, it is expected that this can be a treatment or prevention of type 2 diabetes, in particular, a basic treatment for severe type-2 diabetes, for which blood sugar should be controlled by the insulin supplement therapy.

Furthermore, an agonist or antagonist inhibiting binding of the IRR ligand and IRR can be screened by using the IRR ligand. That is, an agonist or antagonist of the IRR ligand can be screened by allowing binding of the IRR ligand and IRR in the presence of a test substance and measuring inhibition of the binding. For example, as a specific method of searching for the agonist or antagonist, there can be mentioned a method to see whether a biological response caused by adding the IRR ligand to an IRR-expressing cell shows any difference in the presence or absence of the test substance, a method in which inhibition of binding of the IRR ligand labeled with a radioactive substance, fluorescent substance or the like and an IRR-expressing cell or IRR prepared from such a cell is measured in the presence or absence of the test substance, and so forth. Further, modification to biochemical reaction such as phosphorylation caused by addition of the IRR ligand to IRR prepared from a cell membrane of the IRR-expressing cell can also be used as a marker.

Further, as performed in the examples described later, the extracellular domain protein of IRR (soluble IRR) prepared by a genetic recombination method or the like can be immobilized on an appropriate solid phase and inhibition of binding of the IRR ligand thereto can also be used as a marker. Specifically, for example, a sensor chip to which soluble IRR is bound and a sensor chip to which no substance or immunoglobulin or soluble IR is bound are prepared for a surface plasmon resonance (SPR) measuring apparatus. Then, a solution of test substance is flown before, concurrently with and after an IRR ligand solution and a substance suppressing a change in SPR shift specific to the IRR-binding sensor chip by the IRR ligand can be searched to identify a low molecular weight agonist or antagonist with favorable sensitivity. As described above, any methods may be employed so long as modification or inhibition of the IRR-specific reaction induced by the IRR ligand can be detected.

The IRR ligand used as searching means is not limited to the proteins described in the examples of the present specification so long as it is an epithelin/granulin family protein binding to IRR.

In the present invention, when the IRR ligand is used as means for searching for an agonist or antagonist thereof, a solvent and so forth are not particularly limited in general, although it depends on the evaluation method. The concentration is usually in a range of 1 pg/ml to 1 g/ml, more preferably 1 ng/ml to 1 mg/ml, further preferably 10 ng/ml to 10 ìg/ml.

In the present invention, when the IRR ligand or an agonist or antagonist thereof is used as a therapeutic agent, it is administered as an injection (intravenous, subcutaneous, intramuscular injections etc.) or oral preparation. While its dose may vary depending on symptoms, but the dose range is usually in 1 pg to 1 g per day for an adult.

The IRR ligand or an agonist or antagonist thereof can be made into pharmaceutical preparations including injection, inhalant, tablet, granule, powder, capsule, suppository and so forth in a conventional manner. For example, when an injection is prepared, a pH regulator, buffer, stabilizer, preservative and so forth are added to the active ingredient as required.

The IRR ligand or an agonist or an antagonist thereof can be used combined with other pharmaceutical preparation, for example, the drugs for diabetes, neuropathy, renal disorder and/or gastrointestinal injury.

BEST MODE FOR CARRYING OUT THE INVENTION

Hereafter, the present invention will be explained more specifically with reference to the following examples.

EXAMPLE 1

Purification of IRR Ligand From Rat C6 Cell Culture Supernatant

<1> Collection of Cell Culture Supernatant

Rat C6 cells (ATCC No. CCL-107) was suspended in 400 ml of nucleic acid-containing á-MEM medium containing 10% of FCS (fetal calf serum) at an initial density of $3 \times 10^4$ cells/ml. The cells were sealed and cultured in a roller bottle (Falcon 3007) at 37° C. with rotation at a velocity of 0.5 rounds/minute. After culture for three days, the medium was removed, and 400 ml of nucleic acid-containing á-MEM medium with 100 ng/ml of TPA (phorbol 12-myristate 13-acetate) was added. The cells were further cultured for 72 hours and then the culture supernatant was collected.

<2> Purification of IRR Ligand

The culture supernatant in an amount of 1.95 L was added with 1.95 ml of TFA (trifluoroacetic acid) and loaded on a reverse phase column (diameter: 5 cm×length: 7.6 cm, 150 ml/YMC C4 300A S-40 (YMC Co.)). The column was washed with 300 ml of 0.1% TFA, and eluted with 300 ml of 20% acetonitrile/0.1% TFA.

Figure 1:
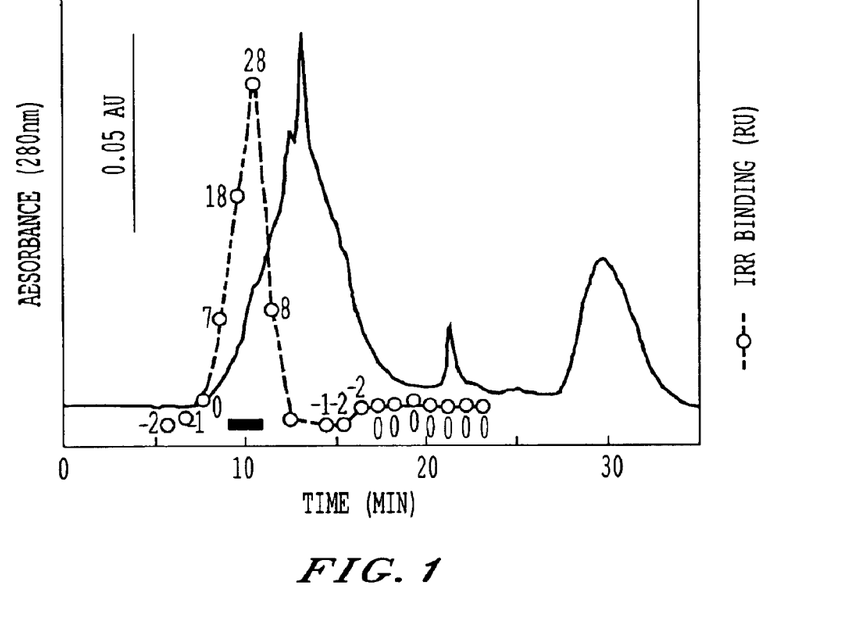
FIG. 1 shows the elution pattern of the crude IRR-ligand preparation (20% acetonitrile eluate of C6 cell culture supernatants) from an HPLC column (diameter: 10 mm×length: 250 mm, Cosmosil 5TMS-300), and IRR binding activities of the fractions, described in Example 1.

The IRR binding activity of the 20% elution fraction was confirmed by the measurement method described later, and then the fraction was diluted with 2-fold amount of 0.1% TFA, adsorbed on an HPLC column (diameter: 10 mm×length: 250 mm, Cosmosil 5TMS-300 (Nakarai Tesque)), sufficiently washed with 0.1% TFA containing 8% of acetonitrile, and then eluted with an acetonitrile concentration gradient (1.6%/minute). The flow rate was adjusted to 3 ml/minute, and 3-ml fractions were collected. The HPLC chromatogram is shown in FIG. 1. The IRR binding activity was collected mainly in the fractions indicated with black bold lines (FIG. 1).

Figure 2:
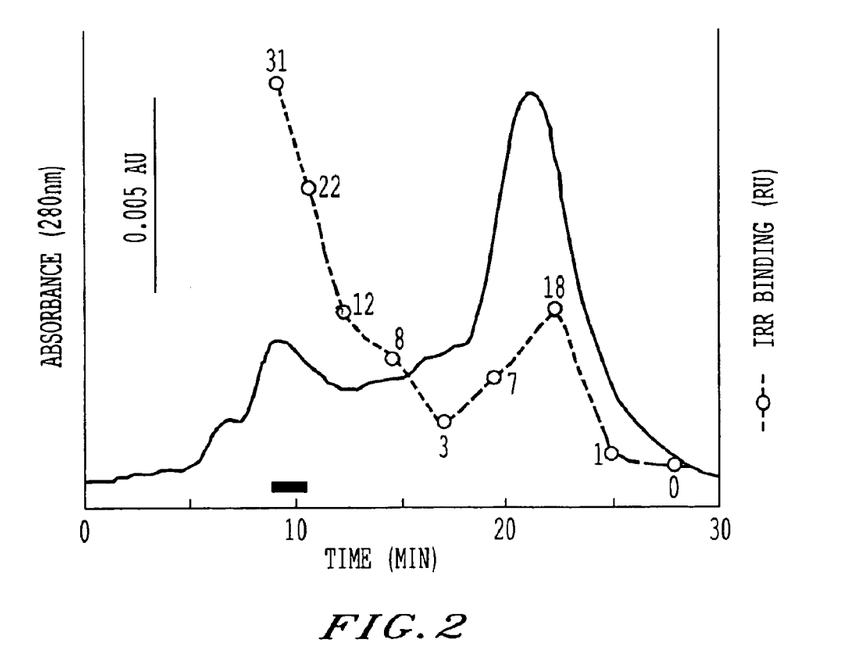
FIG. 2 shows the elution pattern of the half-purified IRR-ligand preparation (pool of fractions 10 and 11 shown in FIG. 1) from an HPLC column (diameter: 4.6 mm×length: 250 mm, Cosmosil 5TMS-300), and IRR binding activities of the fractions, described in Example 1.

The aforementioned active fraction was diluted with 2-fold amount of 0.1% TFA, adsorbed on an HPLC column (diameter: 4.6 mm×length: 250 mm, Cosmosil 5TMS-300), sufficiently washed with 0.1% TFA containing 8% of acetonitrile, and then eluted with an acetonitrile concentration gradient (0.8%/minute). The flow rate was 1 ml/minute, and a peak observed at 280 nm was fractionated by visual inspection. The HPLC chromatogram of this elution is shown in FIG. 2. The IRR binding activity was collected mainly in the fractions indicated with black bold lines (FIG. 2).

Figure 3:
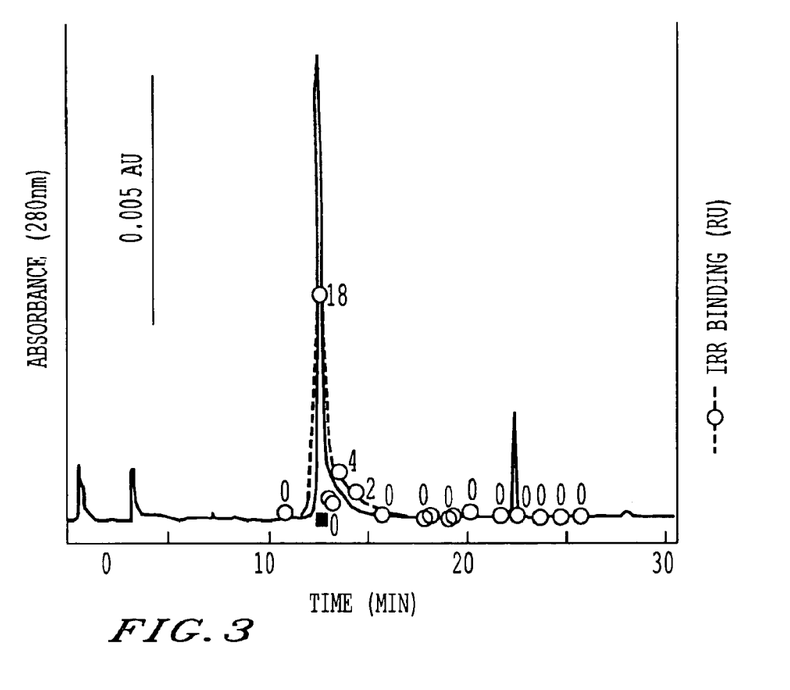
FIG. 3 shows the elution pattern of the half-purified IRR-ligand preparation (fraction 1 shown in FIG. 2) from an HPLC column (diameter: 4.6 mm×length: 250 mm, Vydac 218TP54), and IRR binding activities of the fractions, described in Example 1.

The aforementioned active fraction was diluted with 2-fold amount of 0.1% TFA, adsorbed on an HPLC column (diameter: 4.6 mm×length: 250 mm, Vydac 218TP54 (Vydac)), sufficiently washed with 0.1% TFA containing 8% of acetonitrile, and then eluted with an acetonitrile concentration gradient (1.6%/minute). The flow rate was adjusted to 1 ml/minute, and a peak observed at 280 nm was fractionated by visual inspection. The HPLC chromatogram of this elution is shown in FIG. 3. The IRR binding activity was collected mainly in the fractions indicated with black bold lines (FIG. 3).

<3> Measurement of IRR Binding Activity

In each of the aforementioned purification steps, the IRR binding activity was measured as follows.

(1) Specimen for Measurement

In an amount of 40 µg of bovine serum albumin (BSA) was added as carrier to a solution of test specimen and frozen, and then the solvent was removed by using Speed-Vac AS290A (Savant Instruments). The residue was dissolved in 200 µl of 1 mM hydrochloric acid and neutralized with 200 µl of 2×HBS (40 mM HEPES, 0.6% NaCl, 12 mM EDTA (pH 7.5)) to prepare a test specimen for measurement.

In the last two steps in the purification process, the amounts of dissolved solution and neutralized solution were adjusted to 100 µl, and the addition amount of BSA was 20 µg.

(2) Preparation of Soluble IRR and Soluble IR

Mouse IRR cDNA was cloned from a pancreatic β-cell strain bHC9/MIN6 cDNA library by using a cDNA fragment of the kinase region of mouse IRR amplified by PCR as a probe (Hirayama et al., *Diabetes*, 48, 1237–1244, 1999).

Then, an IRR-Fc fusion protein expression plasmid expressing a protein consisting of IRR fused to H-chain C (constant) region (Fc region) of human IgG1 was constructed by replacing the Fas fragment of pFas-FcII vector (Suda et al., *J. Exp. Med.*, 179, 873–879, 1994, provided by Dr. Takashi Suda, Kanazawa University, Cancer Laboratory) with an extracellular region of mouse IRR (1–920th residues). As a control, an IR-Fc fusion protein expression plasmid was similarly produced by replacing the Fas fragment of pFas-FcII vector with the extracellular region of human IR (1–944th residues) by using human IR cDNA (Kaburagi et al., *J. Biol. Chem.*, 268, 16610–16622, 1993, provided by Dr. Yasushi Kaburagi, University of Tokyo, Medical Department). These plasmids were transfected into CHO cells in a conventional manner, and the cells were cultured in a medium containing G418 to select resistant clones. A clone secreting the target fusion protein into supernatant was selected by Western blotting using anti-human IgG antibodies.

These recombinant CHO cells were cultured until they became confluent ($1-2\times10^7$/dish) in a 10-cm culture dish (Falcon 3003A), and then the medium was changed with 20 ml of HamF-12 medium (serum- and G418-free). After 48–72 hours, the supernatant was sterilely collected. Further, fresh HamF-12 medium was added to the cells to repeat similar culture (3 cycles at most), and then the supernatant was collected. The culture supernatant was concentrated 30 to 100 times by passing it through a regenerated cellulose membrane (PLGCOMP04) using Minitan System (Millipore), and then the IRR-Fc and IR-Fc fusion proteins were purified in a conventional manner by using a protein A column (Amersham Pharmacia, HiTrap Protein A, 1 ml).

(3) Evaluation of IRR Binding Activity by Surface Plasmon Resonance (SPR) Measurement SPR measurement was performed by using BIACORE 2000 (Biacore).

Each flow cell of CM5 sensor chip was activated with EDC/NHS (mixture of N'-(3-dimethylaminopropyl) carbodiimide hydrochloride and N-hydroxysuccinimide) in a conventional manner (flow rate: 5 µl, 7 minutes), and IRR-Fc (20 µg/ml, 10 mM acetate buffer (pH 3.9)) or IR-Fc (20 µg/ml, 10 mM formate buffer (pH 3.7)) were each allowed to bind to separate flow cells by the amine coupling method.

The flow rate as adjusted to 10 µl/minute, and 30 µl of measurement sample was loaded. SPR (resonance units: RU) was measured 20 seconds before the injection of sample (baseline) and 165 seconds after the start of the injection (15 seconds before the finish of the injection, bound 1). The chip was regenerated by washing it with 10 µl of 10 mM Glycine-HCl (pH 2.35), and a following sample was measured after the baseline was stabilized.

For every sample, binding activities of IRR-Fc immobilized flow cell [bound 1−baseline] and binding activities of IR-Fc immobilized flow cell [bound 1−baseline] were calculated, and difference obtained by subtracting the IR-Fc binding value from the IRR-Fc binding value was used as binding value of the sample.

The binding values are represented with circles and numerals in the description and FIGS. 1–3.

EXAMPLE 2

Determination of N-terminus Amino Acid Sequence of IRR Ligand

The N-terminal amino acid sequence of the IRR binding activity fraction sample purified in Example 1 was determined by using a protein sequencer 476A (Applied Biosystems) according to the method using a glass filter treated with polybrene described in the instructions book of the apparatus. First, 45 µl of the active fraction sample shown in FIG. 3 was added to a glass filter treated with polybrene according to the method of the instruction book to perform amino acid sequence analysis.

PTH amino acids considered to correspond to the amino acids derived from the sample for the 1–22nd residues, and the detected amounts thereof calculated from peak heights for PTH amino acid specimens are shown in Table 1.

TABLE 1

| Residue No. | Amino acid (detected amount: pmol) | | | |
|---|---|---|---|---|
| 1 | Ile | (15.9) | Asp | (12.1) |
| 2 | Gly | (12.5) | Ile | (19.0) |
| 3 | | | Gly | (16.6) |
| 4 | Asp | (7.8) | | |
| 5 | Gln | (10.9) | Asp | (11.9) |

TABLE 1-continued

| Residue No. | Amino acid (detected amount: pmol) | | | |
|---|---|---|---|---|
| 6 | His | (5.9) | Gln | (15.1) |
| 7 | Thr | (4.9) | His | (7.8) |
| 8 | | | Thr | (5.6) |
| 9 | Pro | (6.0) | | |
| 10 | Val | (6.1) | Pro | (9.3) |
| 11 | Gly | (3.3) | Val | (8.9) |
| 12 | Gln | (5.6) | Gly | (9.0) |
| 13 | Thr | (2.8) | Gln | (8.7) |
| 14 | | | Thr | (3.1) |
| 15 | | | | |
| 16 | Pro | (3.5) | | |
| 17 | | | Pro | (6.0) |
| 18 | Leu | (3.1) | | |
| 19 | Lys | (2.9) | Leu | (5.1) |
| 20 | Gly | (3.4) | Lys | (4.4) |
| 21 | | | Gly | (4.6) |
| 22 | | | | |

From the above results, the N-terminus amino acid sequence of the aforementioned active fraction sample was considered to consist of a mixture of a peptide having the amino acid sequence of SEQ ID NO: 1 at the N-terminus and a peptide having the amino acid sequence of SEQ ID NO: 2 at the N-terminus. Xaa in each sequence was considered to be a cysteine residue that are not detected under the above condition or a serine or threonine residue showing a low yield under the above condition.

Proteins showing homology to the aforementioned amino acid sequence were searched from a database (NBRF) by using Amino Acid Sequence Homology (GENETYX). As a result, the following proteins were retrieved as proteins showing homology of 50% or more.

Epithelin/granulin precursor—mouse

Epithelin/granulin precursor—rat

Acrogranin—mouse

Granulin—rat

Granulin precursor—human

Because the cells used for the purification of IRR ligand (C6 cells) were derived from rat, the rat epithelin/granulin precursor (589 amino acid residues) was compared with the amino acid sequences of SEQ ID NOS: 1 and 2. As a result, the sequence of SEQ ID NO: 1 corresponded to sequence of the 440–460th residues of the rat epithelin/granulin precursor, and the sequence of SEQ ID NO: 2 corresponded to the sequence of the 439–460th amino acid residues of the same.

EXAMPLE 3

Re-Purification of IRR Ligand

Figure 4:
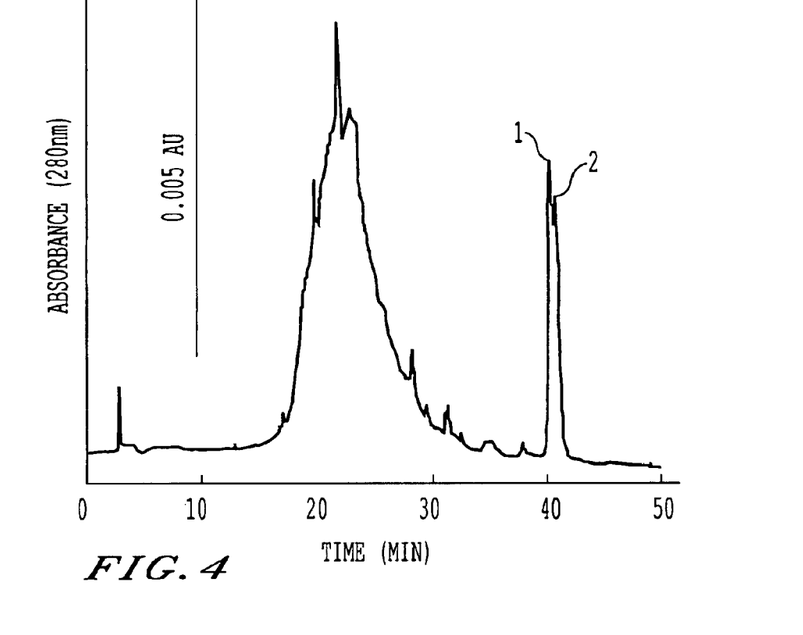
FIG. 4 shows the elution pattern of active fractions in final purification step from an HPLC column (diameter: 4.6 mm×length: 250 mm, Vydac 218TP54), described in Example 3.

IRR ligand was newly purified from 4 L of culture supernatant of rat C6 cells, which were cultured in the same manner as in Example 1. A half amount (400 µl) of the crude active fraction, which was fractionated stepwise from the culture supernatant by using YMC C4 300A S-40, Cosmosil 5TMS-300 and Vydac 218TP54 in the same manner as in Example 1, was diluted with 1.2 ml of 0.05% HFBA (heptafluorobutyric acid), adsorbed on an HPLC column (diameter: 4.6 mm×length: 250 mm, Vydac 218TP54), sufficiently washed with 0.05% HFBA containing 8% of acetonitrile, and then eluted with an acetonitrile concentration gradient (1%/minute for 30 minutes, and 0.5%/minute thereafter). The flow rate was adjusted to 1 ml/minute, and a peak at 280 nm was fractionated by visual inspection. The HPLC chromatogram of this elution is shown in FIG. 4. The binding activity was collected in the fractions indicated with arrows (Peaks 1 and 2, FIG. 4). Further, Peaks 1 and 2 were separately re-purified under the same conditions, and concentrated to 150–200 µl by using Speed-Vac. About 1/10 amount of each re-purified specimen (about 10 µg) was lyophilized and dissolved in 200 µl of buffer, and the binding activity was measured. As a result, a binding activity of 13 RU was observed for Peak 1 and 21 RU for Peak 2.

By using 30 µl each of Peaks 1 and 2 of the purified fractions shown in FIG. 4, amino acid sequence analysis was performed. The 1–22th residues were analyzed, and as a result, the amino acid sequence of SEQ ID NO: 2 was obtained from Peak 1, and an amino acid sequence corresponding to the amino acid sequence of SEQ ID NO: 1 was obtained from Peak 2.

EXAMPLE 4

Determination of Molecular Weight of IRR Ligand by Mass Spectrometry

In an amount of 10 µl of methanol and 4 µl of acetic acid were added to 10 µl of a sample of the active fraction shown in FIG. 3, and spectrum was measured by the GADT-microelectrospray ion method using Fourier-transformation ion cyclotron mass analyzer APEXII70e (Bruker Daltonics). For mass calibration, bovine insulin, bovine ubiquitin and chicken lysozyme were used.

As a result, main peaks of m/z=2045.6716, 1534.7963, 1228.0888 and 1023.3715 were observed, and because they corresponded to $[M+3H]^{+3}$, $[M+4H]^{+4}$, $[M+5H]^{+5}$ and $[M+6H]^{+6}$, respectively, the molecular weight was presumed to be 6135. Combining the results of Example 2, it was considered that the main component of the active fraction shown in FIG. 3 was a protein having the amino acid sequence of SEQ ID NO: 3 consisting of the residues of from the 439th aspartic acid as the N-terminus to the 495th lysine as the C-terminus of the rat epithelin/granulin precursor, or a protein having the amino acid sequence of SEQ ID NO: 4 consisting of the residues of from the 440th isoleucine as the N-terminus to the 496th aspartic acid as the C-terminus of the same.

DIGCDQHTSCPVGQTCCPSLKGSWAC-CQLPHAVCCEDRQHCCPAGYTCNVKARTCE K (SEQ ID NO: 3)

IGCDQHTSCPVGQTCCPSLKGSWACCQL-PHAVCCEDRQHCCPAGYTCNVKARTCE KD (SEQ ID NO: 4)

Further, since there were also found sub-peaks of m/z= 1563.5479, 1581.2989 and 1552.5515 corresponding to $[M+4H]^{+4}$, the molecular weights of the proteins corresponding to them were presumed to be 6250, 6321 and 6206, respectively. Combining the results of Example 2, it was considered that the active fraction shown in FIG. 3 contained, as minor components, a protein having the amino acid sequence of SEQ ID NO: 5, 6 or 7 having the 439th or 440th amino acid residue of the rat epithelin/granulin precursor as the N-terminus.

DIGCDQHTSCPVGQTCCPSLKGSWAC-CQLPHAVCCEDRQHCCPAGYTCNVKARTCE KD (SEQ ID NO: 5)

DIGCDQHTSCPVGQTCCPSLKGSWAC-CQLPHAVCCEDRQHCCPAGYTCNVKARTCE KDA (SEQ ID NO: 6)

IGCDQHTSCPVGQTCCPSLKGSWACCQL-PHAVCCEDRQHCCPAGYTCNVKARTCE KDA (SEQ ID NO: 7)

In addition, it is presumed that 12 cysteine residues contained in each of the aforementioned proteins were crosslinked in the molecule.

Further, by using 10 μl each of Peaks 1 and 2 of the purified fraction shown in FIG. 4, molecular weight was similarly determined. As a result, it was presumed that Peak 1 consisted of, as the main peaks, proteins having molecular weights of 6250 and 6321 and the amino acid sequences of SEQ ID NOS: 5 and 6.

Furthermore, Peak 2 was presumed to consist of a protein, as the main peak, a protein having a molecular weight of 6135 and the amino acid sequence of SEQ ID NO: 4.

---

What is claimed is:

1. An isolated protein consisting of the amino acid sequence set forth in SEQ ID NO: 4.

2. A pharmaceutical composition, which comprises the protein of claim 1 and one or more pharmaceutically acceptable additives.

3. The pharmaceutical composition according to claim 2, wherein said one or more pharmaceutically acceptable additives is selected from the group consisting of a pH regulator, a buffer, a stabilizer, and a preservative.

4. The pharmaceutical composition according to claim 2, wherein said protein is in an amount of 1 pg to 1 g.

5. The pharmaceutical composition according to claim 2, wherein said composition is in a preparation form selected from the group consisting of an injection, an inhalant, a tablet, a granule, a powder, a capsule, and a suppository.

6. An isolated protein, which has a binding activity to an insulin receptor-related receptor and the following characteristics:
   (a) the protein consists of the amino acid sequence of SEQ ID NO: 4
   (b) the protein has a molecular weight of about 6135, 6206, 6250 or 6321 measured by mass spectrometry using the Fourier transformation ion cyclotron method.

7. An isolated protein, which binds to an insulin receptor-related receptor, wherein the protein consists of an amino acid sequence selected from the group consisting of:
   an amino acid sequence of SEQ ID NO: 4,
   an amino acid sequence of SEQ ID NO: 3,
   an amino acid sequence of SEQ ID NO: 5,
   an amino acid sequence of SEQ ID NO: 6, and
   an amino acid sequence of SEQ ID NO: 7.

8. A pharmaceutical composition, which comprises the protein of claim 7 and one or more pharmaceutically acceptable additives.

9. The pharmaceutical composition according to claim 8, wherein said one or more pharmaceutically acceptable additives is selected from the group consisting of a pH regulator, a buffer, a stabilizer, and a preservative.

10. The pharmaceutical composition according to claim 8, wherein said protein is in an amount of 1 pg to 1 g.

11. The pharmaceutical composition according to claim 8, wherein said composition is in a preparation form selected from the group consisting of an injection, an inhalant, a tablet, a granule, a powder, a capsule, and a suppository.

* * * * *